US012324704B2

(12) United States Patent
McLaughlin et al.

(10) Patent No.: US 12,324,704 B2
(45) Date of Patent: Jun. 10, 2025

(54) SECUREMENT OF HANDS-FREE ULTRASOUND PROBE

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 13 days.

(21) Appl. No.: 17/549,470

(22) Filed: Dec. 13, 2021

(65) Prior Publication Data

US 2022/0183657 A1    Jun. 16, 2022

Related U.S. Application Data

(60) Provisional application No. 63/125,380, filed on Dec. 14, 2020.

(51) Int. Cl.
*A61B 8/00*    (2006.01)
*A61B 8/08*    (2006.01)

(52) U.S. Cl.
CPC .......... *A61B 8/4236* (2013.01); *A61B 8/0891* (2013.01); *A61B 8/4227* (2013.01); *A61B 8/4281* (2013.01)

(58) Field of Classification Search
CPC ............................ A61B 8/4227; A61B 8/4281
See application file for complete search history.

(56) References Cited

U.S. PATENT DOCUMENTS

| | | | |
|---|---|---|---|
| 5,148,809 A | 9/1992 | Biegeleisen-Knight et al. | |
| 5,181,513 A | 1/1993 | Touboul et al. | |
| 5,325,293 A | 6/1994 | Dorne | |
| 5,441,052 A | 8/1995 | Miyajima | |
| 5,549,554 A | 8/1996 | Miraki | |
| 5,573,529 A | 11/1996 | Haak et al. | |
| 5,676,159 A * | 10/1997 | Navis ................... | A61B 8/4281 128/849 |
| 5,775,322 A | 7/1998 | Silverstein et al. | |

(Continued)

FOREIGN PATENT DOCUMENTS

| | | |
|---|---|---|
| EP | 0933063 A1 | 8/1999 |
| EP | 1504713 A1 | 2/2005 |

(Continued)

OTHER PUBLICATIONS

PCT/US12/61182 International Seach Report and Written Opinion dated Mar. 11, 2013.

(Continued)

*Primary Examiner* — Boniface N Nganga
(74) *Attorney, Agent, or Firm* — Rutan & Tucker LLP

(57) ABSTRACT

Disclosed herein is an ultrasound probe securement device to secure an ultrasound probe to a patient. The securement device can include a probe coupling mechanism to couple an ultrasound probe to the securement device, a patient coupling mechanism to couple the securement device to a patient, and a constraining mechanism to maintain an acoustic coupling of the ultrasound probe with the patient during an ultrasound procedure without user intervention.

13 Claims, 11 Drawing Sheets

(56) References Cited

U.S. PATENT DOCUMENTS

| | | |
|---|---|---|
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,261,231 B1 * | 7/2001 | Damphousse ....... G10K 11/004 600/459 |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childers et al. |
| 2006/0015039 A1 | 1/2006 | Cassidy et al. |
| 2006/0079781 A1 | 4/2006 | Germond-Rouet et al. |
| 2006/0184029 A1 | 8/2006 | Haim et al. |
| 2006/0184074 A1 * | 8/2006 | Vaezy ................ A61K 41/0028 601/2 |
| 2006/0210130 A1 | 9/2006 | Germond-Rouet et al. |
| 2007/0043341 A1 | 2/2007 | Anderson et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0208060 A1 * | 8/2008 | Murkin .................... A61B 8/06 600/459 |

(56) References Cited

U.S. PATENT DOCUMENTS

| | | |
|---|---|---|
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0211026 A2 | 8/2010 | Sheetz et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0040190 A1* | 2/2011 | Jahnke .............. A61B 8/12 600/459 |
| 2011/0071404 A1 | 3/2011 | Schmitt et al. |
| 2011/0113886 A1* | 5/2011 | Elejalde ........... A61B 8/4281 73/644 |
| 2011/0230793 A1* | 9/2011 | Larson .............. A61N 7/02 601/2 |
| 2011/0313293 A1 | 12/2011 | Lindekugel et al. |
| 2012/0179038 A1 | 7/2012 | Meurer et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2014/0005530 A1 | 1/2014 | Liu et al. |
| 2014/0073976 A1 | 3/2014 | Fonte et al. |
| 2014/0100440 A1 | 4/2014 | Cheline et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0126871 A1* | 5/2015 | Yoon ............... A61B 8/467 600/459 |
| 2015/0209113 A1 | 7/2015 | Burkholz et al. |
| 2015/0209526 A1 | 7/2015 | Matsubara et al. |
| 2015/0297097 A1 | 10/2015 | Matsubara et al. |
| 2015/0359991 A1 | 12/2015 | Dunbar et al. |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0166232 A1 | 6/2016 | Merritt |
| 2016/0199027 A1* | 7/2016 | Scully .............. A61B 8/4281 424/9.5 |
| 2016/0202053 A1 | 7/2016 | Walker et al. |
| 2016/0213398 A1 | 7/2016 | Liu |
| 2016/0278869 A1 | 9/2016 | Grunwald |
| 2016/0296208 A1 | 10/2016 | Sethuraman et al. |
| 2016/0302765 A1 | 10/2016 | Liu et al. |
| 2016/0374644 A1 | 12/2016 | Mauldin, Jr. et al. |
| 2017/0079548 A1 | 3/2017 | Silverstein et al. |
| 2017/0164923 A1 | 6/2017 | Matsumoto |
| 2017/0215842 A1 | 8/2017 | Ryu et al. |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0153513 A1* | 6/2018 | Mauldin, Jr. ............ G09G 5/36 |
| 2018/0153515 A1 | 6/2018 | Song et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0263597 A1 | 9/2018 | Tchang et al. |
| 2019/0269943 A1 | 9/2019 | Lewis, Jr. et al. |
| 2019/0365348 A1* | 12/2019 | Toume ................. A61B 8/065 |
| 2020/0113540 A1 | 4/2020 | Gijsbers et al. |
| 2022/0039777 A1 | 2/2022 | Durfee |
| 2022/0096797 A1 | 3/2022 | Prince |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |

FOREIGN PATENT DOCUMENTS

| | | |
|---|---|---|
| EP | 1591074 B1 | 5/2008 |
| EP | 3181083 A1 | 6/2017 |
| EP | 3643242 A1 | 4/2020 |
| JP | 2000271136 A | 10/2000 |
| JP | 2018175547 A | 11/2018 |
| JP | 2018175548 A * | 11/2018 |
| KR | 20180070878 A | 6/2018 |
| WO | 2013059714 A1 | 4/2013 |
| WO | 2014/115150 A1 | 7/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020/067897 A1 | 4/2020 |
| WO | 2020/186198 A1 | 9/2020 |
| WO | 2022/072727 A2 | 4/2022 |
| WO | 2022/081904 A1 | 4/2022 |

OTHER PUBLICATIONS

PCT/US2021/049123 filed Sep. 3, 2021 International Search Report and Written Opinion dated Feb. 4, 2022.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.

(56) References Cited

OTHER PUBLICATIONS

U.S. Appl. No. 17/020,476, filed Sep. 14, 2020 Non-Final Office Action dated Feb. 9, 2022.
Lu Zhenyu et al."Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/063129 filed Dec. 13, 2021 International Search Report and Written Opinion dated Mar. 10, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.
William F Garrett et al.: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

\* cited by examiner

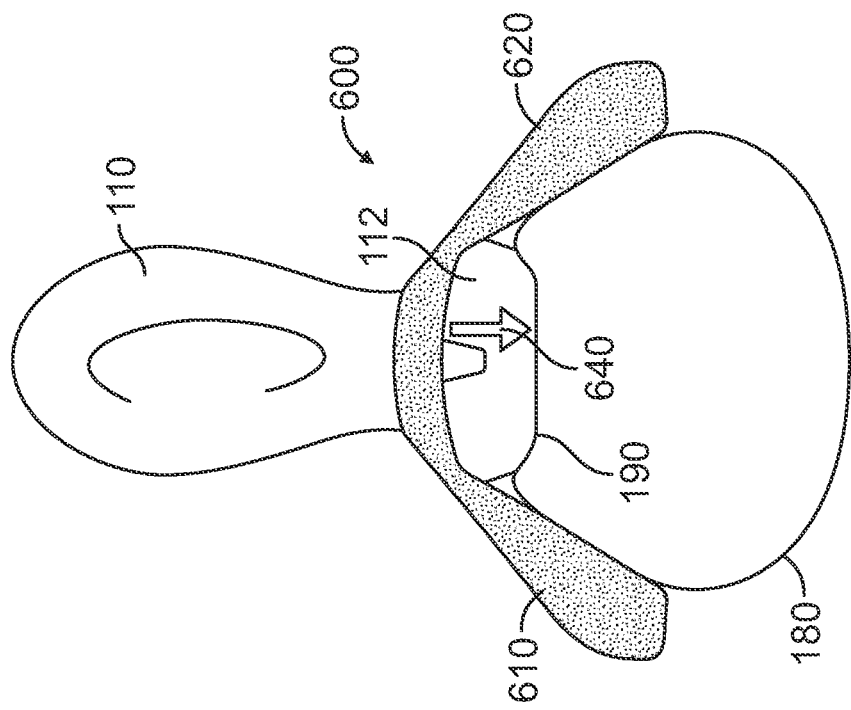
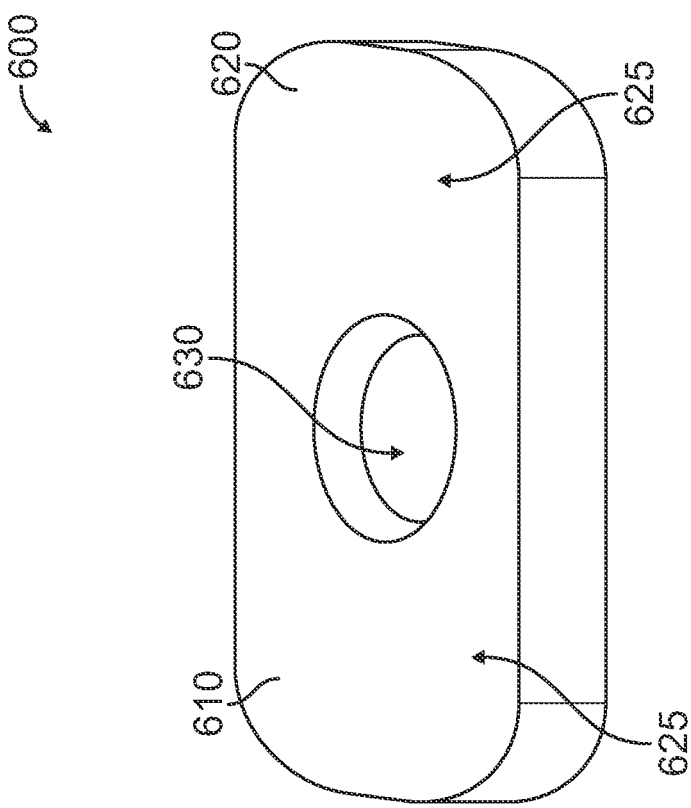
FIG. 6B
FIG. 6A

SECUREMENT OF HANDS-FREE ULTRASOUND PROBE

PRIORITY

This application claims the benefit of priority to U.S. Provisional Application No. 63/125,380, filed Dec. 14, 2020, which is incorporated by reference in its entirety into this application.

BACKGROUND

There are currently a variety of existing ultrasound imaging systems that include ultrasound probes connected to visual displays. The ultrasound imaging systems may be used by a clinician to provide imaging of one or more blood vessels in accordance the placement of a medical device, e.g., a catheter, into a patient. In some instances, the clinician may manually establish a position of an ultrasound probe to facilitate imaging of a defined portion of the patient. In further instances, the clinician may manually maintain the established probe position during a medical procedure. In some instances, such as the insertion of a catheter, it may be awkward or difficult for a single clinician to manually maintain the position of the probe and simultaneously perform the medical procedure. For example, a clinician may need to perform the medical procedure with one hand while maintaining the location and orientation of the probe with the other hand. In some instances, it may be advantageous for a clinician to use both hands to perform the medical procedure. For example, it may be advantageous for a clinician to use both hands to precisely insert a needle into a target vein while viewing ultrasound images. Similarly, in some instances, the clinician may need to perform a task away from the patient, while obtaining ultrasound images. As such, there is a need for maintaining an ultrasound probe position in the absence of clinician intervention with the probe.

Disclosed herein are embodiments of devices and methods for the securement of an ultrasound probe in relation to a patient to enable hands-free ultrasound imaging of the patient.

SUMMARY OF THE INVENTION

Briefly summarized, disclosed herein is an ultrasound probe securement device to secure an ultrasound probe to a patient. The securement device includes a probe coupling mechanism to couple an ultrasound probe to the securement device, a patient coupling mechanism to couple the securement device to a patient; and a constraining mechanism to maintain an acoustic coupling of the ultrasound probe with the patient during an ultrasound procedure without user intervention.

In some embodiments, ultrasound signals from the ultrasound probe pass through the securement device into the patient. In some embodiments, the securement device comprises an acoustic coupling material to facilitate transmission of ultrasound signals through the securement device.

The securement device may be configured to constrain the ultrasound probe in an established location and/or orientation with respect to the patient. In some embodiments, the securement device is configured to maintain acoustic coupling of the ultrasound probe with the patient during ultrasound imaging of a blood vessel and/or during insertion of a medical device into the blood vessel.

In some embodiments, the probe coupling mechanism comprises a frame, the frame including at least one clip member to attach the securement device to the ultrasound probe, and the patient coupling mechanism comprises an adhesive layer configured to attach the securement device to the patient. In some embodiments, at least a portion of the adhesive layer includes acoustic coupling material.

In some embodiments, the securement device includes a top frictional surface configured to inhibit sliding displacement of the ultrasound probe with respect to the securement device, and a bottom frictional surface configured to inhibit sliding displacement of the securement device with respect to the patient.

In some embodiments, the securement device comprises a container including acoustic coupling material. The container may also include elevated density material to facilitate coupling of the securement device to the patient via a gravitational force. The container may include an outer compartment containing the elevated density material. In some embodiments, the outer compartment comprises a first outer compartment extending away from the ultrasound probe on a first side and a second outer compartment extending away from the ultrasound probe on a second side opposite the first side, and wherein the first outer compartment and the second outer compartment contain the elevated density material. In some embodiments, the container comprises an inner compartment containing the acoustic coupling material.

In some embodiments, the securement device comprises one or more securement straps configured to extend around a portion of the patient.

In some embodiments, the securement device comprises a circumferential wall configured to 1) extend between the ultrasound probe and the patient, 2) couple to the ultrasound probe at a top end of the circumferential wall, and 3) sealably couple to the patient at a bottom end of the circumferential wall to define a closed compartment between the ultrasound probe and the patient. The securement device may maintain an acoustic coupling of the ultrasound probe with the patient when a vacuum is present within the closed compartment. The circumferential wall may include a bellows configured to bias the circumferential wall toward an extended state to at least partially define the vacuum within the closed compartment. The closed compartment may also contain acoustic coupling material. The securement device may further include a lateral wall coupled to an inside surface of the circumferential wall. The lateral wall extends across the closed compartment to define a top end of the closed compartment. The lateral wall may comprise acoustic coupling material.

Also disclosed herein is an ultrasound imaging system comprising an ultrasound probe including a user interface and a probe housing, a display, a console operatively coupled to the ultrasound probe and the display, the console configured for processing ultrasound signals and rendering ultrasound images on the display, and a securement device configured to maintain acoustic coupling of the ultrasound probe with a patient during use of the ultrasound imaging system.

In some embodiments of the system, the user interface includes a user interface housing that is separate from the probe housing, and the ultrasound probe is operably coupled to the user interface. In some embodiments, the user interface and the display are both disposed within the probe housing. In some embodiments, the display is attached to the ultrasound probe and the display is pivotably attached to the ultrasound probe.

In some embodiments of the system, the probe housing includes a height dimension extending away from the patient during use and a lateral dimension extending along the patient during use, wherein the lateral dimension is greater than the height dimension.

In some embodiments of the system, the securement device comprises acoustic coupling material and the securement device may include a container (e.g., a bag) containing the acoustic coupling material. The container may also contain elevated density material.

In some embodiments of the system, the securement device is configured to maintain acoustic coupling of the ultrasound probe with the patient via a suction force.

In some embodiments of the system, the securement device includes a top frictional surface configured to inhibit sliding displacement of the ultrasound probe with respect to the securement device and a bottom friction surface configured to inhibit sliding displacement of the securement device with respect to the patient.

Also disclosed herein is a method of using an ultrasound imaging system. The method comprises obtaining an ultrasound imaging system where the ultrasound imaging system includes an ultrasound probe, a user interface, a display, and a console operatively coupled to the ultrasound probe, the user interface, and the display. The console is configured for processing ultrasound signals and rendering ultrasound images on the display. The method further includes coupling the ultrasound probe to a securement device and coupling the securement device to a patient, where the securement device comprises acoustic coupling material.

In some embodiments, the further method includes manually positioning the ultrasound probe with respect to the patient to establish acoustic coupling of the ultrasound probe with the patient.

In some embodiments of the method, the securement device is configured to constrain the ultrasound probe in the established position without user intervention, and wherein the method further comprises constraining the ultrasound probe in the established position with the securement device.

In some embodiments, the method further includes obtaining ultrasound images of a blood vessel while the ultrasound probe is constrained by the securement device, and the method may further include inserting a medical device into the blood vessel while the ultrasound probe is constrained by the securement device.

In some embodiments of the method, the securement device comprises a top frictional surface configured to inhibit sliding displacement of the ultrasound probe with respect to the securement device and a bottom frictional surface configured to inhibit sliding displacement of the securement device with respect to the patient.

In some embodiments of the method, the securement device comprises a container (e.g., a bag) containing the acoustic coupling material. The container may be coupled to the ultrasound probe and the container may include a first compartment extending away from the ultrasound probe on a first side and a second compartment extending away from the ultrasound probe on a second side opposite the first side. The first compartment and the second compartment contain elevated density material.

In some embodiments of the method, the securement device is configured to establish a closed compartment between the ultrasound probe and the patient, and the method may further comprise applying a downward force on the ultrasound probe to expel contents out of the closed compartment so that upon release of the downward force a vacuum is formed within the closed compartment to constrain the ultrasound probe in the established position without user intervention.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 6A provides a top perspective view of a securement device comprising a container with multiple compartments, in accordance with some embodiments.

FIG. 6B provides a cross-sectional view of a securement of FIG. 6A in use with an ultrasound probe, in accordance with some embodiments.

DETAILED DESCRIPTION

Figure 1A:
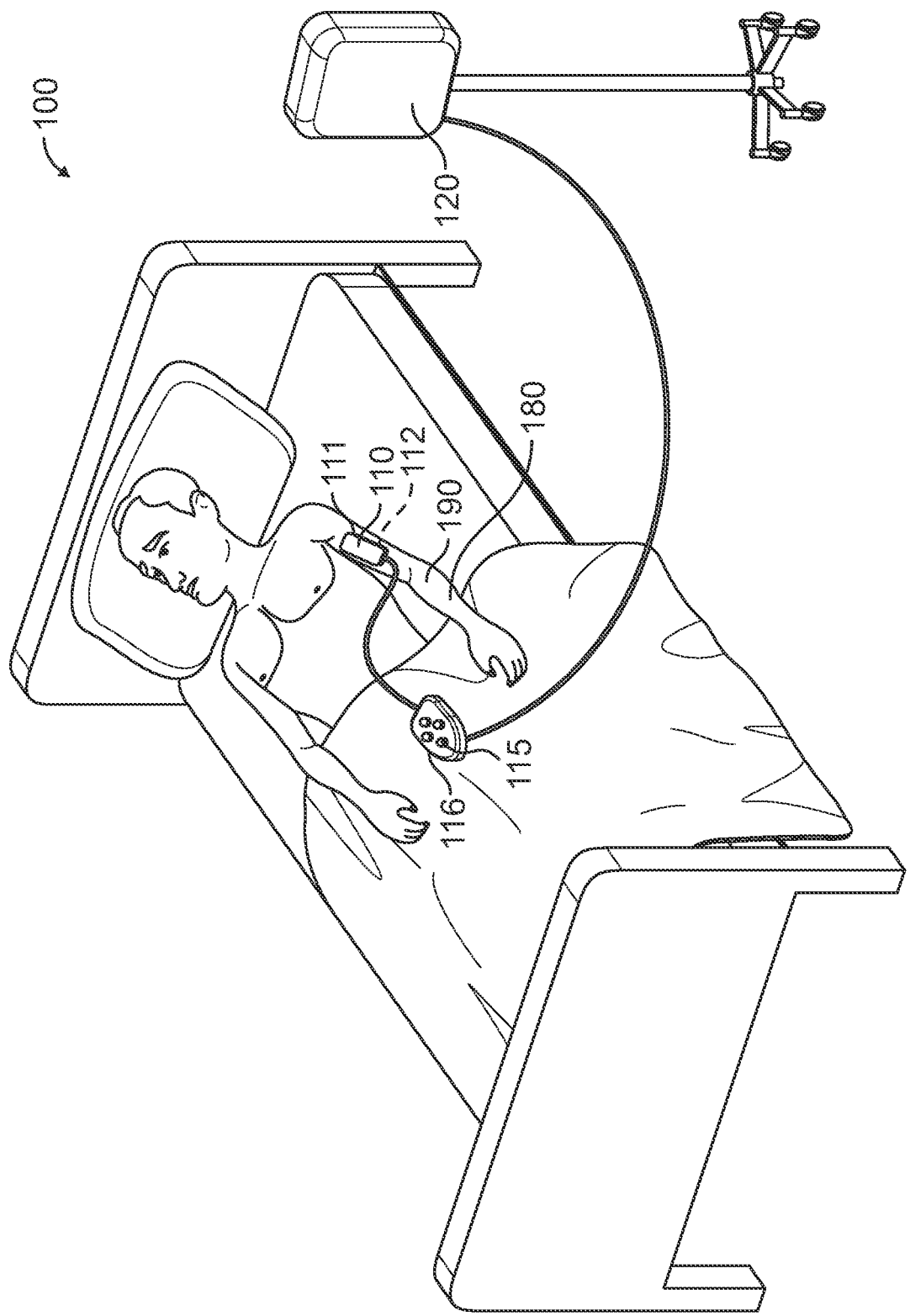
FIG. 1A provides a view of an ultrasound environment including an ultrasound imaging system having an ultrasound probe secured to a patient, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising."

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

Embodiments disclosed herein are directed to an ultrasound probe securement device to be used with an ultrasound imaging system to enable a clinician to perform additional tasks such as placing a needle into a patient while obtaining ultrasound images. In particular, embodiments disclosed herein enable an ultrasound probe to remain stationary in an established position, i.e., location and/or orientation, in relation to the patient without manual contact (intervention) by the clinician. The securement device may also acoustically couple the ultrasound probe to the skin of the patient.

In some embodiments, the securement device may be integral to the ultrasound probe and as such, may be configured for multiple use across different patients. In other embodiments, the securement device may be separate from the ultrasound probe. Still, the separate securement device may be configured for multiple use across patients or single use, i.e., disposable. According to some embodiments, the ultrasound imaging system may be configured to capture ultrasound images of a medical device insertion site. In some embodiments, the ultrasound imaging system may be configured to provide real-time imaging of a needle in relation to a target blood vessel.

In some embodiments, the ultrasound probe may include an integrated or detachable needle guide, such as the needle guide as described, for example, in U.S. Pat. No. 10,863,970, titled "Needle Guide Including Enhanced Visibility Entrance," filed Dec. 23, 2014, which is incorporated by reference in its entirety herein. In some embodiments, the securement device may couple to or otherwise engage with the needle guide. The ultrasound imaging system, according to the exemplary embodiments, may be used during insertion of a catheter to ensure proper placement, where examples of such catheters include, but are not limited to, Peripherally Inserted Central Catheters (PICCs) or Peripheral Intravenous Catheters (PIVCs). Such systems may also be utilized during subsequent indwell assessments.

In some instances, an acoustic coupling material, e.g., a gel substance, is used to enhance the acoustic coupling of an ultrasound probe with the skin of a patient. A clinician may apply a gel to a head of the ultrasound probe or to the skin of the patient to establish an acoustic coupling between the probe head and the skin. In some instances, the presence of space and/or air pockets between the probe head and the skin will diminish, inhibit, or eliminate acoustic coupling. An acoustic coupling material may be any material that is substantially incompressible, such as water, for example. The acoustic coupling material may be a solid, a liquid, a gel or a combination thereof.

Referring to FIG. 1A, a view of an ultrasound environment including an ultrasound imaging system 100 having an ultrasound probe 110 secured to an extremity 180 of a patient, in accordance with some embodiments, is shown. The ultrasound imaging system 100 includes the ultrasound probe 110 connected to an ultrasound imaging device 120. In some embodiments, the ultrasound probe 110 may have a needle guide (not shown) attached to the probe 100. The ultrasound imaging system depicted in FIG. 1A is capable of ultrasound imaging of a blood vessel within a patient and, in some embodiments, needle tracking imaging in combination with the blood vessel imaging. The ultrasound imaging system 100 may be used for needle insertion or for insertion site assessment or for anatomic scanning.

As shown in FIG. 1A, the ultrasound imaging system 100 may include a user interface 115 coupled to the ultrasound probe 110 and the display 120. In some embodiments, the ultrasound probe 110, user interface 115, and the display 120 may be coupled to together via a wired connection. In other embodiments, the ultrasound probe 110, user interface 115, and the display 120 may be wirelessly coupled together. The user interface 115 may include one or more buttons and the clinician may manipulate the user interface 115 to operate the ultrasound imaging system 100. In use, the user interface 115 may be selectively positioned in close proximity to or away from the ultrasound probe 110 and/or the display 120 as may be convenient for the clinician. In some embodiments, the user interface 115 may comprise a user interface housing 116.

The ultrasound probe 110 comprises a probe housing 111. The ultrasound probe 110 includes ultrasonic transducers (not shown) and may include other electrical components (not shown) disposed within the housing 111.

In use, a probe head 112 of the ultrasound probe 110 may be placed in contact with the skin 190 of the patient so that the ultrasound probe 110 may transmit ultrasound signals into the patient. The clinician may manipulate the ultrasound probe 110 to establish or enhance acoustic coupling of the probe head 112 with the skin 190. In other words, the clinician may manipulate the ultrasound probe 110 to remove any space and/or air pockets between the probe head 112 and the skin 190 of the patient. In some instances, the clinician may place an acoustic coupling material (sometimes referred to as acoustic transparent material), e.g., a gel-like substance, between the head 112 and skin 190 to facilitate or enhance the transmission of ultrasound signals.

In some embodiments, the probe housing 111 may be shaped to inhibit positional alteration via contact with items such as clothing, bedding, etc. In such embodiments, the probe housing 111 may comprise a low profile as illustrated in FIG. 1A. In some embodiments, the ultrasound probe 110 may comprise a height dimension extending away from the patient that is less than one or more lateral dimensions extending along the patient.

Figure 1C:
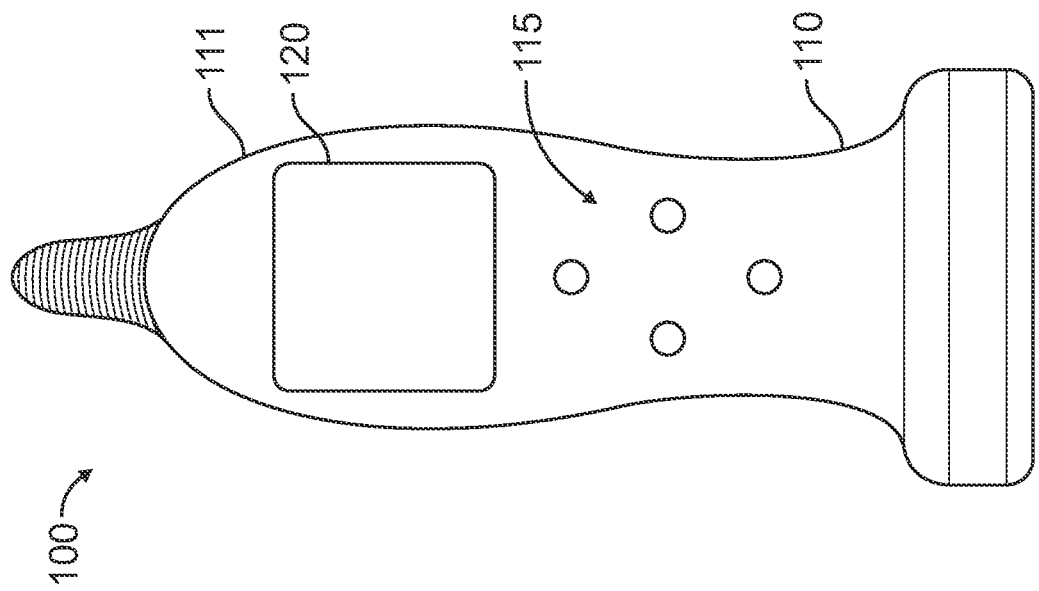
FIG. 1C provides a view of an ultrasound imaging system having an ultrasound probe, the ultrasound probe including an operator interface and a display enclosed in a single probe housing, in accordance with some embodiments.
Figure 1B:
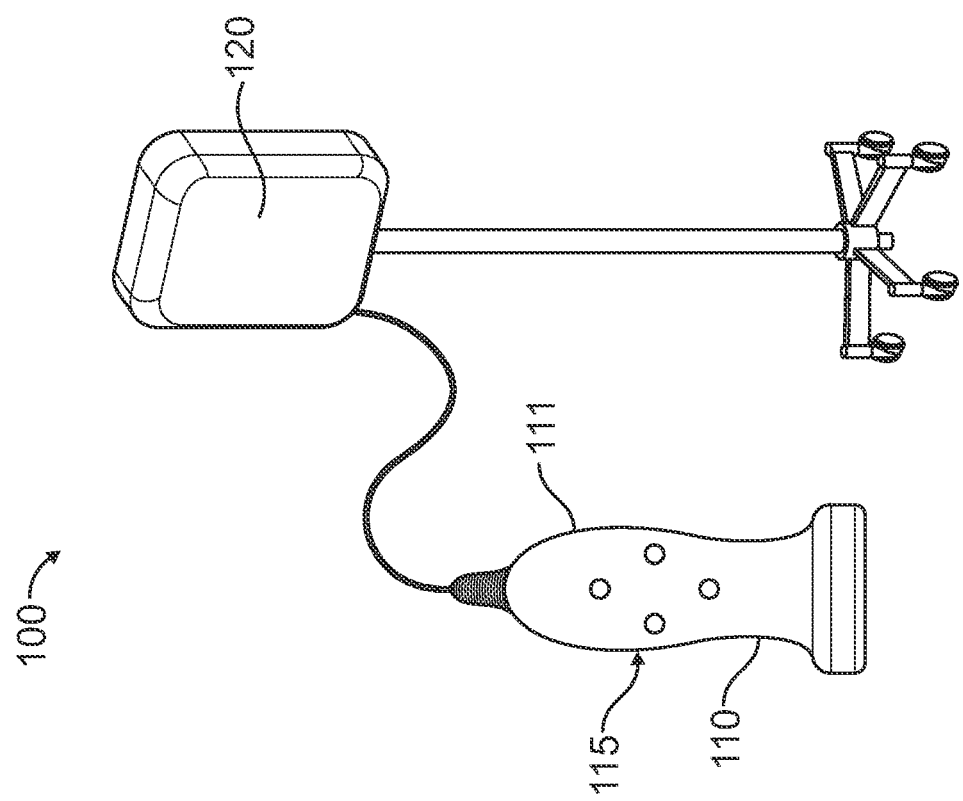
FIG. 1B provides a view of an ultrasound imaging system having an ultrasound probe with an integrated operator interface coupled to a display, in accordance with some embodiments.

In some embodiments as shown in FIG. 1B, the ultrasound probe 110 may integrally include the user interface 115. In other words, the user interface 115 may be included within the probe housing 111. In some embodiments, the ultrasound probe 110/user interface 115 combination may be coupled to the display 120 via a wired connection. In other embodiments, the ultrasound probe 110/user interface 115 combination may be wirelessly coupled to the display 120.

In some embodiments, the probe housing 111 may be shaped for grasping and manual manipulation by the clinician. In some embodiments, the probe housing 111 may be shaped to facilitate the application of a downward force of the ultrasound probe 110 against the patient. The probe housing 111 may be shaped to aid the clinician in rotating or otherwise adjusting an orientation of the ultrasound probe 110. In some embodiments, the ultrasound probe 110 may comprise a height dimension extending away from the patient that is greater than one or more lateral dimensions, extending along the patient.

In some embodiments as shown in FIG. 1C, the ultrasound probe 110 may integrally include the user interface 115 and the display 120. In other words, the user interface 115 and the display 120 may be included within the probe housing 111.

Figure 1D:
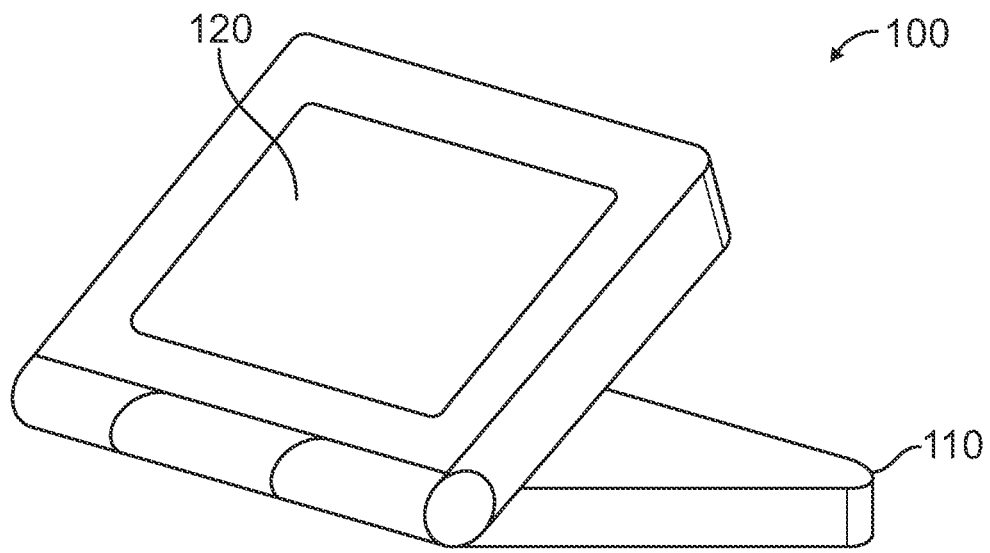
FIG. 1D provides a view of an ultrasound imaging system having a display pivotably attached to an ultrasound probe, in accordance with some embodiments.

In some embodiments as shown in FIG. 1D, the display 120 may be pivotably attached to the ultrasound probe 110. In use the clinician may pivot the display 120 at an angle to facilitate viewing of the display 120 from a convenient direction. In some embodiments, may be pivotably positioned between a storage position where the display 120 is disposed parallel to the ultrasound probe 110, i.e., at an angle of "0" zero degrees with respect to the probe, and an upright position where the display 120 is disposed perpendicular to the ultrasound probe 110, i.e., at an angle of 90 degrees to the ultrasound probe 110. In some embodiments, the display 120 may be pivotably positioned between an angle of 90 degrees and 180 degrees with respect to the probe.

Figure 1E:
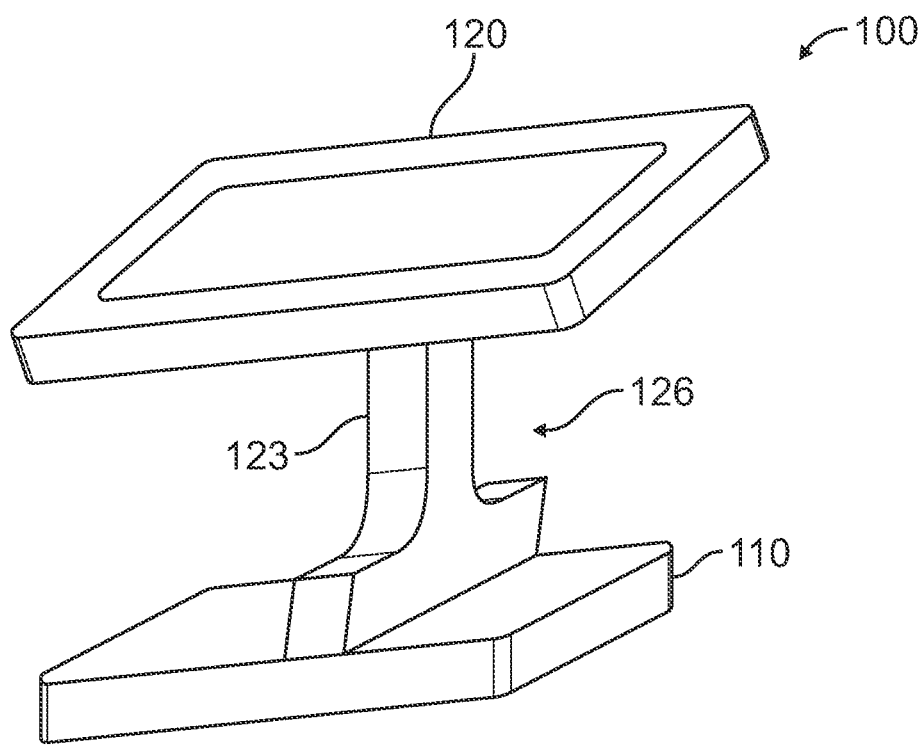
FIG. 1E provides a view of an ultrasound imaging system having a display attached to an ultrasound probe via a post, in accordance with some embodiments.

In some embodiments as shown in FIG. 1E, the display 120 may be attached to the ultrasound probe 110 via a post 123. The post 123 may comprise one or more finger grips 126. The display 120 may be attached to the post 126 at a fixed orientation. In some embodiments, the display 120 may be attached to the post 126 via a ball and socket mechanism (not shown) to allow the clinician to adjust the orientation of the display 120 with respect to the ultrasound probe 110.

Figure 2A:
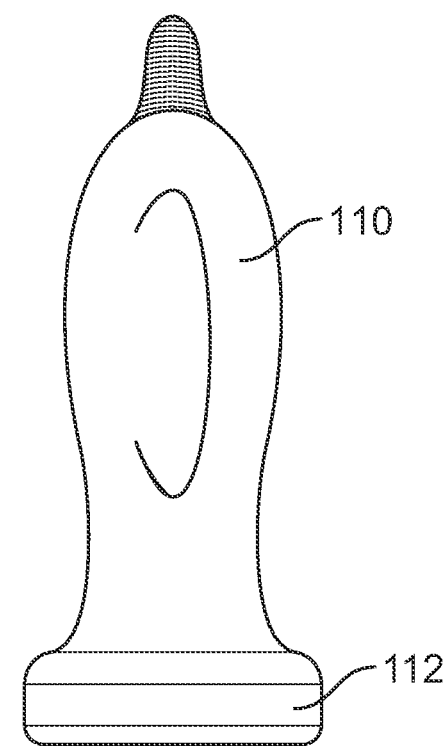
FIG. 2A provides a side view of an ultrasound probe and a securement device including an adhesive layer, in accordance with some embodiments.
Figure 2A:
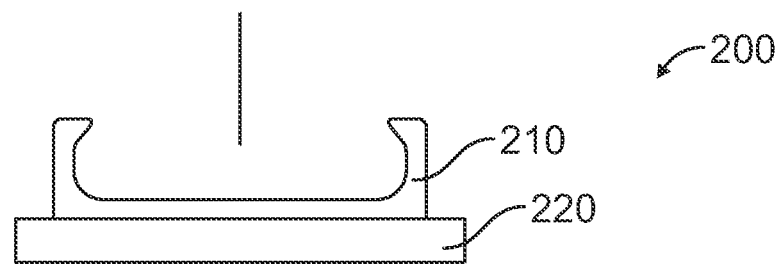
Figure 2B:
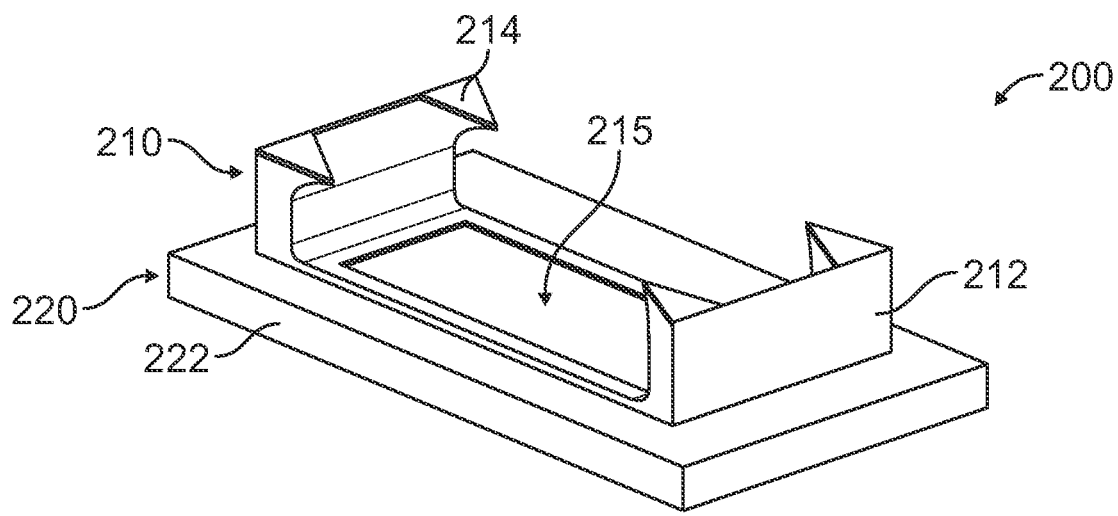
FIG. 2B provides a perspective view of the securement device of FIG. 2A, in accordance with some embodiments.

FIGS. 2A and 2B illustrate a securement device 200 configured to be attached to the ultrasound probe 110, in accordance with some embodiments. FIG. 2A shows a front view of a securement device 200 separated from the ultrasound probe 110. FIG. 2B is perspective view of the securement device 200. The securement device 200 comprises a probe coupling mechanism 210 and a patient coupling mechanism 220. The probe coupling mechanism 210 comprises a frame 212 including one or more clips 214 configured to clip onto the ultrasound probe 110 at the probe head 112. The ultrasound probe 110 may comprise one or more of a depression, a ledge, a protrusion or the like to facilitate clip-on attachment of the securement device 200 to the ultrasound probe 110. After use, the securement device 200 may be unclipped, or otherwise separated from the ultrasound probe 110.

The patient coupling mechanism 220 comprises an adhesive layer 222. The adhesive layer is attached to the frame 212. The adhesive layer 222 may comprise an acoustic coupling material. In some embodiments, the adhesive layer 222 may extend radially outward from the frame 212 as shown in FIG. 2B. In other embodiments, the adhesive layer 222 may be disposed within a circumference of the frame 212. The frame 212 includes an opening 215 to facilitate direct contact between the probe head 112 and the adhesive layer 222. In some embodiments, the adhesive layer 222 may be configured to not adhere to the probe head 112. The adhesive layer 222 may be pliable so that a clinician may alter the shape of the adhesive layer 222 to conform to the skin surface of the patient. Altering the shape of the adhesive layer 222 may establish or enhance acoustic coupling of the probe head 112 with the skin 190.

In some embodiments, the adhesive layer 222 may be comprise a pressure adhesive including a backing paper. In such an embodiment, the adherence of the adhesive layer 222 may be enabled by removal of the backing paper. The adhesive layer 222 may be configured to adhere to the skin 190 of the patient. In some embodiments, the adhesive layer 222 may be formed of an adhesive that is one or more of biocompatible, acoustically conductive (or has a low acoustic interference), and/or includes a high coefficient of friction. In some embodiments, after use, the adhesive layer 222 may be separated from the frame 212 and replaced with a new adhesive layer 222.

Figure 3B:
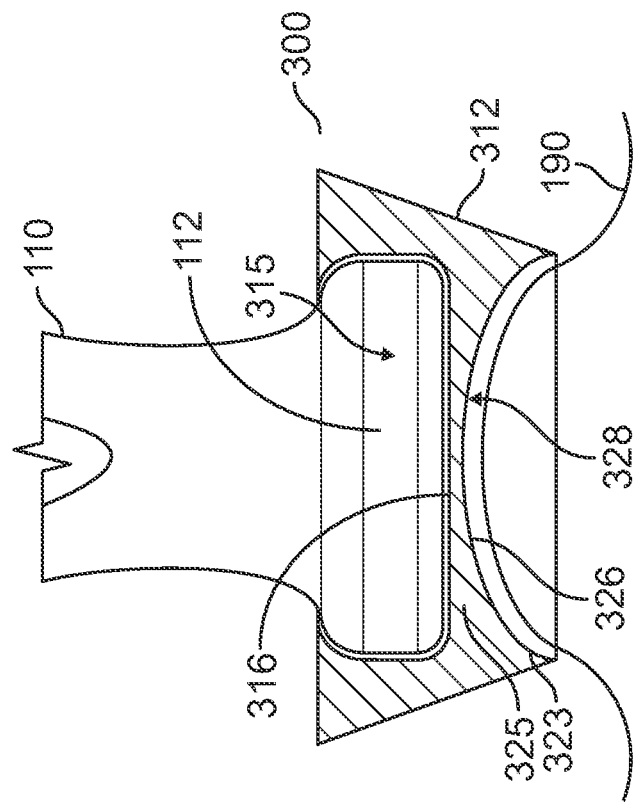
FIG. 3B is a cross-sectional view of the securement device of FIG. 3A coupled to an ultrasound probe, in accordance with some embodiments.
Figure 3A:
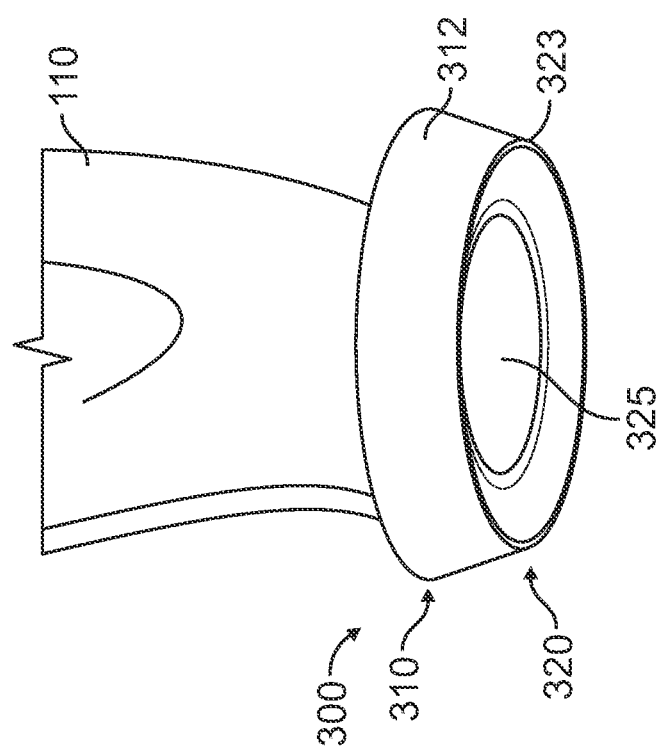
FIG. 3A provides a front perspective view of a securement device configured for coupling an ultrasound probe to a patient via a suction force, in accordance with some embodiments.

FIGS. 3A and 3B illustrate an embodiment of a securement device 300 configured to couple the ultrasound probe 110 to the patient via a suction force. FIG. 3A is front perspective view of securement device 300 attached to the ultrasound probe 110. FIG. 3B is front cross-sectional view of securement device 300 attached to the ultrasound probe 110. The securement device 300 comprises a probe coupling mechanism 310 and a patient coupling mechanism 320. The securement device 300 may be formed of an elastomeric material, such as silicone, polyurethane, rubber or any other suitably flexible material. The probe coupling mechanism 310 may comprise a circumferential wall 312 and a lateral wall 325 (see FIG. 3B) coupled to and extending inward from the circumferential wall 312 to form an upper compartment 315 of the probe coupling mechanism 310. The probe coupling mechanism 310 may be configured to stretch over the probe head 112 so that the probe head 112 is at least partially disposed within the upper compartment 315. A top surface 316 of the lateral wall 325, facing the probe head 112, is shaped to facilitate acoustic coupling with the probe head 112. The lateral wall 325 may comprise an acoustic coupling material.

The patient coupling mechanism 320 of the securement device 300 comprises a lower portion of the circumferential wall 312 including a bottom edge 323. The bottom edge 323 is configured to sealably couple to the skin 190 of patient. As such, the circumferential wall 312, the lateral wall 325, and the skin 190 of the patient form a closed lower compartment 328 when the securement device 300 is applied to the patient. In use, the clinician may apply a downward force on the ultrasound probe 110 to create a positive pressure within the lower compartment 328. The positive pressure may force air, or other contents of the lower compartment 328, to pass between the bottom edge 323 and the skin 190 and exit the lower compartment 328 so that when the downward force is removed, a vacuum is created in the lower compartment 328. The vacuum in the lower compartment 328 produces a suction force between the securement device 300 and the skin 190 thereby securing the ultrasound probe 110 to the patient. In some embodiments, the lower compartment 328 may contain an acoustic coupling material, to establish or enhance acoustic coupling between the probe head 112 and the skin 190. In such an embodiment, acoustic coupling material may be expelled from the lower compartment 328 when the clinician applies the downward force. The bottom surface 326 may be flat, concave, or convex.

Figure 3C:
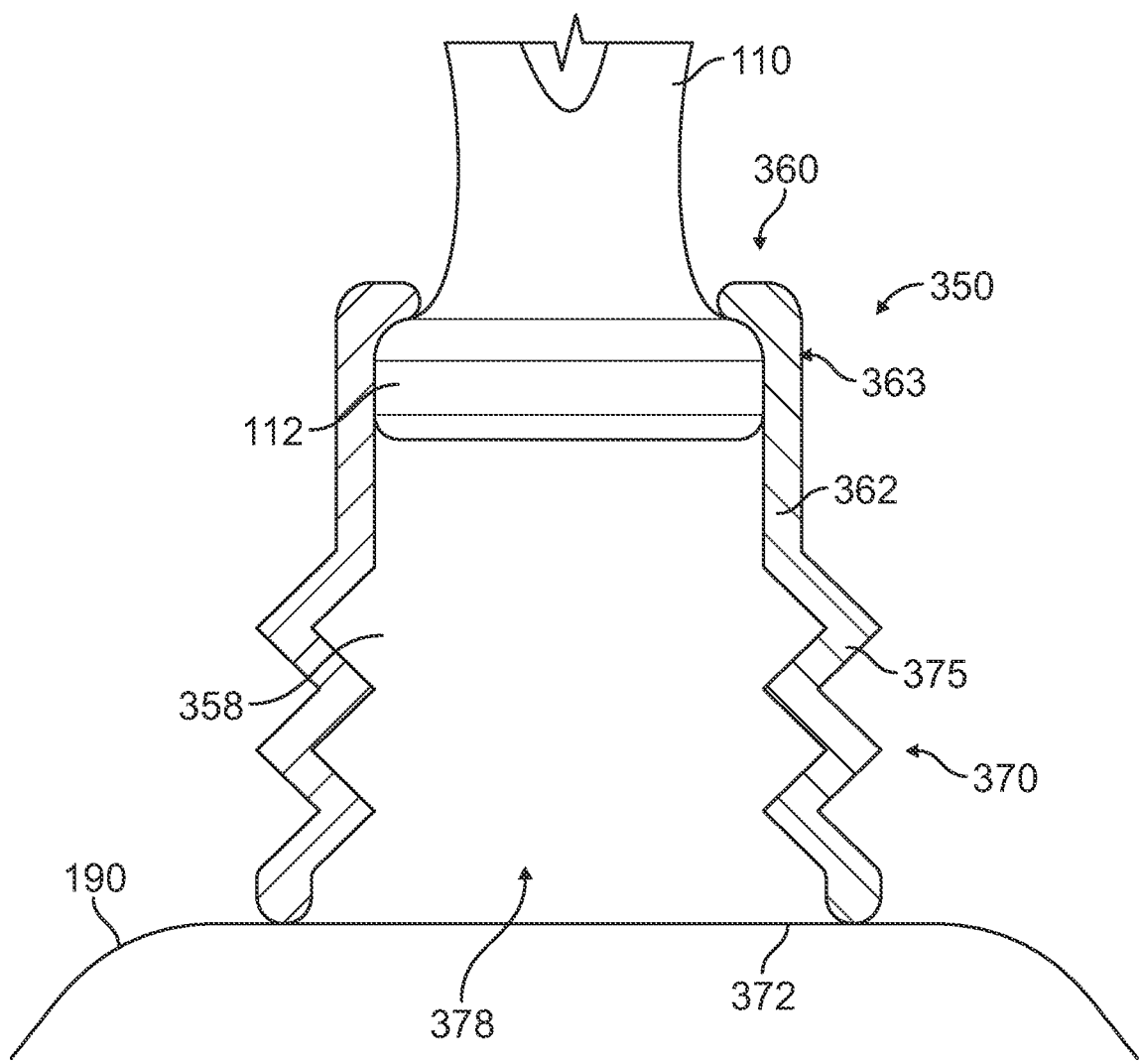
FIG. 3C is a cross-sectional side view of another embodiment of a securement device configured for coupling an ultrasound probe to a patient via a suction force, in accordance with some embodiments.

FIG. 3C is front cross-sectional view of securement device 350 coupled to the ultrasound probe 110, the securement the device 350 is configured to couple the ultrasound probe 110 to the patient via a suction force. The securement device 350 may be formed of an elastomeric material, such as silicone, polyurethane, rubber or any other suitably stretchable material. The probe coupling mechanism 360 comprises a circumferential wall 362 configured to form a stretchable sleeve portion 363. The sleeve portion 363 may be stretched over the probe head 112 to couple to the ultrasound probe 110 and form a seal with the probe head 112.

The securement device 350 comprises a lower portion of the circumferential wall 362 including a bottom edge 372. The bottom edge 372 is configured to sealably couple to the skin 190 of patient. As such, the circumferential wall 362, the probe head 112, and the skin 190 of the patient form a closed compartment 378 when the securement device 350 is applied to the patient. The circumferential wall 362 may be configured to be biased toward an extended state. In some embodiments, the circumferential wall 362 may include a bellows 375 as a biasing member. In use, an acoustic coupling material 358, may be disposed within the compartment 362 before coupling with the patient to establish or enhance acoustic coupling between the probe head 112 and the skin 190. During attachment, the clinician may apply a downward force on the ultrasound probe 110 to compress the circumferential wall 362 and cause acoustic coupling material 358 to pass between the bottom edge 372 and the skin 190 and exit the compartment 378. When the downward force is removed, the circumferential wall 362 may re-extend toward the extended state and cause a vacuum to form within compartment 378. The vacuum in the compartment 328 produces a suction force between the securement device 350 and the skin 190 thereby securing the ultrasound probe 110 to the patient.

Figure 4:
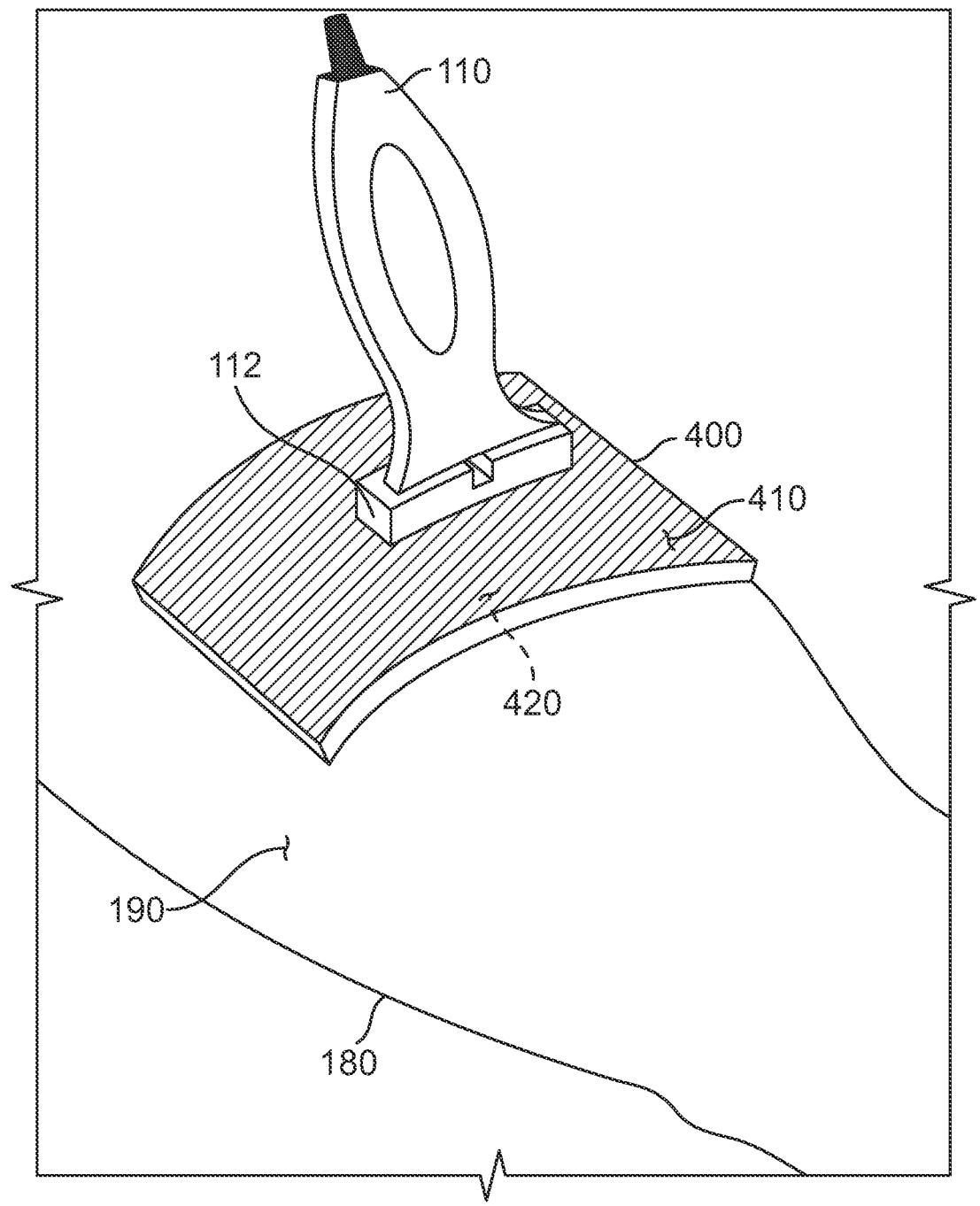
FIG. 4 provides a view of a securement device having top and bottom frictional surfaces in use with an ultrasound probe, in accordance with some embodiments.

FIG. 4 provides a view of securement device 400 in the form of a flexible pad disposed between the ultrasound probe 110 and skin 190 of the patient. The securement device 400 comprises a frictional top surface 411. The frictional top surface 411 may inhibit sliding of the ultrasound probe 110 with respect to the securement device 400. Similarly, the securement device 400 comprises a frictional bottom surface 421. The frictional bottom surface 421 may inhibit sliding of the securement device 400 with respect to the skin 190. In some embodiments, the frictional top surface 411 and/or the frictional bottom surface 421 may include one or more adhesive portions to supplement the frictional surfaces, 411, 421. The securement device 400 may comprise or be formed of an acoustic coupling material. As such, the securement device 400 may acoustically couple the ultrasound probe 110 to the skin 190. In some embodiments, the securement device 400 may comprise an elevated density material.

Figure 5B:
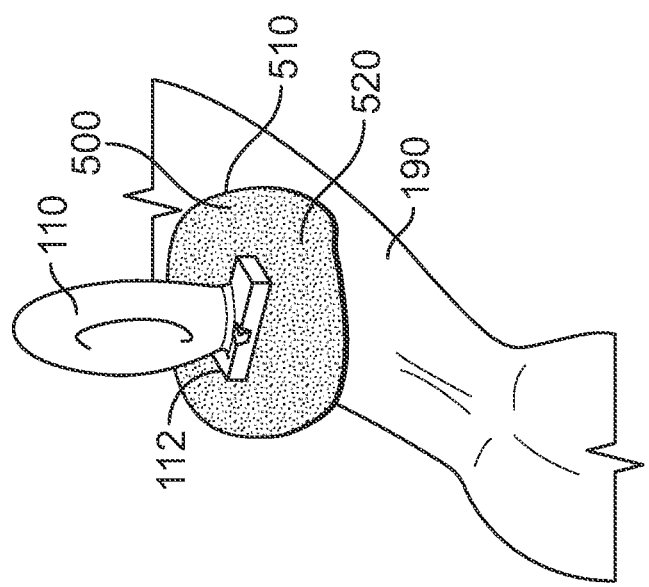
FIG. 5B provides a view of a securement of FIG. 5A in use with an ultrasound probe, in accordance with some embodiments.
Figure 5A:
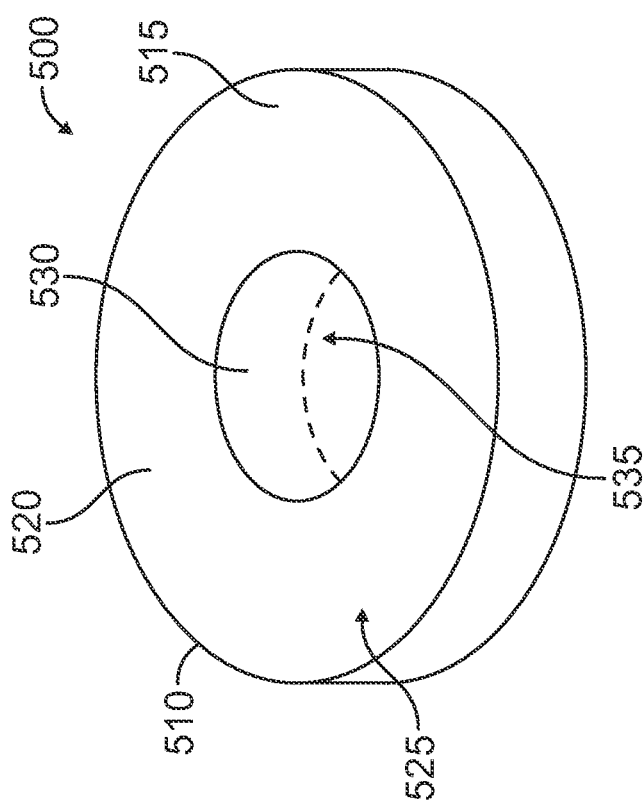
FIG. 5A provides a top perspective view of a securement device comprising a container, in accordance with some embodiments.

FIGS. 5A and 5B illustrate a securement device 500 in the form of a container (e.g., a bag) disposed between the ultrasound probe 110 and skin 190 of the patient. FIG. 5A shows a perspective view of the securement device 500 and FIG. 5B shows the securement device 500 disposed between the ultrasound probe 110 and skin 190 of a patient. The securement device 500 comprises a container 510 defining an outer compartment 520 and an inner compartment 530. In some embodiments, the outer compartment 520 and the inner compartment 530 may be combined to form a single compartment. The container 510 comprises a material that is flexible so that the container 510 may conform to a contour of the patient. In some embodiments, the material may be stretchable and enable acoustic transmission/coupling. One example of such a material is a urethane polymer bag filled with high viscosity acoustic gel. The container 510 may be formed from a flat sheet material or the container 510 may be formed of a material comprising one or more preformed shapes.

The inner compartment 530 may contain an acoustic coupling material 535. In use, the inner compartment 530 may be disposed between the probe head 112 and the skin 190 so that the acoustic coupling material 535 may facilitate transmission of ultrasound signals through the securement device 500 and into the patient. In some embodiments, the inner compartment 530 may comprise a preformed shape such as a central depression in the securement device 500. As such, the inner compartment 530 may be configured to receive at least portion of the probe head 112 and thereby at least partially constrain the location and/or orientation of the ultrasound probe 110 with respect to the securement device 500. In some embodiments, the container 510 may include a frictional outer surface 515 to resist sliding displacement between the securement device 500 and the probe head 112 and between the securement device 500 and the skin 190.

The outer compartment 520 may contain an elevated density material 525. The density of the elevated density material 525 may be between about 0.5 and 1.0 grams per milliliter (g/ml), 1.0 and 1.5 g/ml, 1.5 and 2.0 g/ml, or greater than about 2.0 g/ml. The outer compartment 520 may also contain an acoustic coupling material. The elevated density material 525 may comprise a liquid, a gel, granules, a powder or any combination thereof. In some embodiments, the outer compartment 520 and the inner compartment 530 may be combined to form a single compartment containing acoustic coupling material and/or elevated density material 525.

FIGS. 6A and 6B illustrate a securement device 600 in the form of a container including an opening 630. FIG. 6A shows a perspective view of the securement device 600 and FIG. 6B shows cross-sectional view the securement device 600 in use with the ultrasound probe 110 as may be applied to the extremity 180 of a patient. The securement device 600 comprises at least a first compartment 610 and a second compartment 620 extending laterally away from an opening 630 on opposite sides of the opening 630. The first compartment 610 and the second compartment 620 may be individual flexible portions (e.g., containers) or they may a single portion (e.g., container). The compartments 610, 620 may comprises a material that is flexible so that the compartments 610, 620 may conform to a contour of a patient. In some embodiments, the material may be stretchable. The securement device 600 may be formed from a flat sheet material or the securement device 600 may be formed of a material comprising one or more preformed shapes.

In some embodiments, the opening 630 may be shaped and sized to receive at least a first portion of the ultrasound probe 110 therethrough. In some embodiments, the opening 630 may also be shaped and sized to prevent passage of at least a second portion of the ultrasound probe 110 therethrough. In some embodiments, the opening 630 may be shaped and sized to prevent at least a portion of the probe head 112 from passing through the opening 630. In this exemplary embodiment, the securement device 600 is configured to be placed over the ultrasound probe 110 so that the probe head 112 is constrained between the securement device 600 and the skin 190.

As shown in FIG. 6B, in use, the compartments 610, 620 extend downward on opposite sides of the extremity 180. The securement device 600 may be configured to apply a downward force 640 of the probe head 112 against the skin 190 of the patient. In some embodiments, the downward force 640 may be defined by a weight of the securement device 600 which may be substantially defined by a combined weight of the contents of the compartments 610, 620. The force 640 may be sufficiently high to facilitate obtaining ultrasound images of the patient yet sufficiently low prevent pain to the patient and/or inhibit compression of patient tissue.

The compartments 610, 620 may contain an elevated density material 625. The compartments 610, 620 may also contain an acoustic coupling material. The elevated density material 525 may comprise a liquid, a gel, granules, a powder, or any combination thereof.

Figure 7:
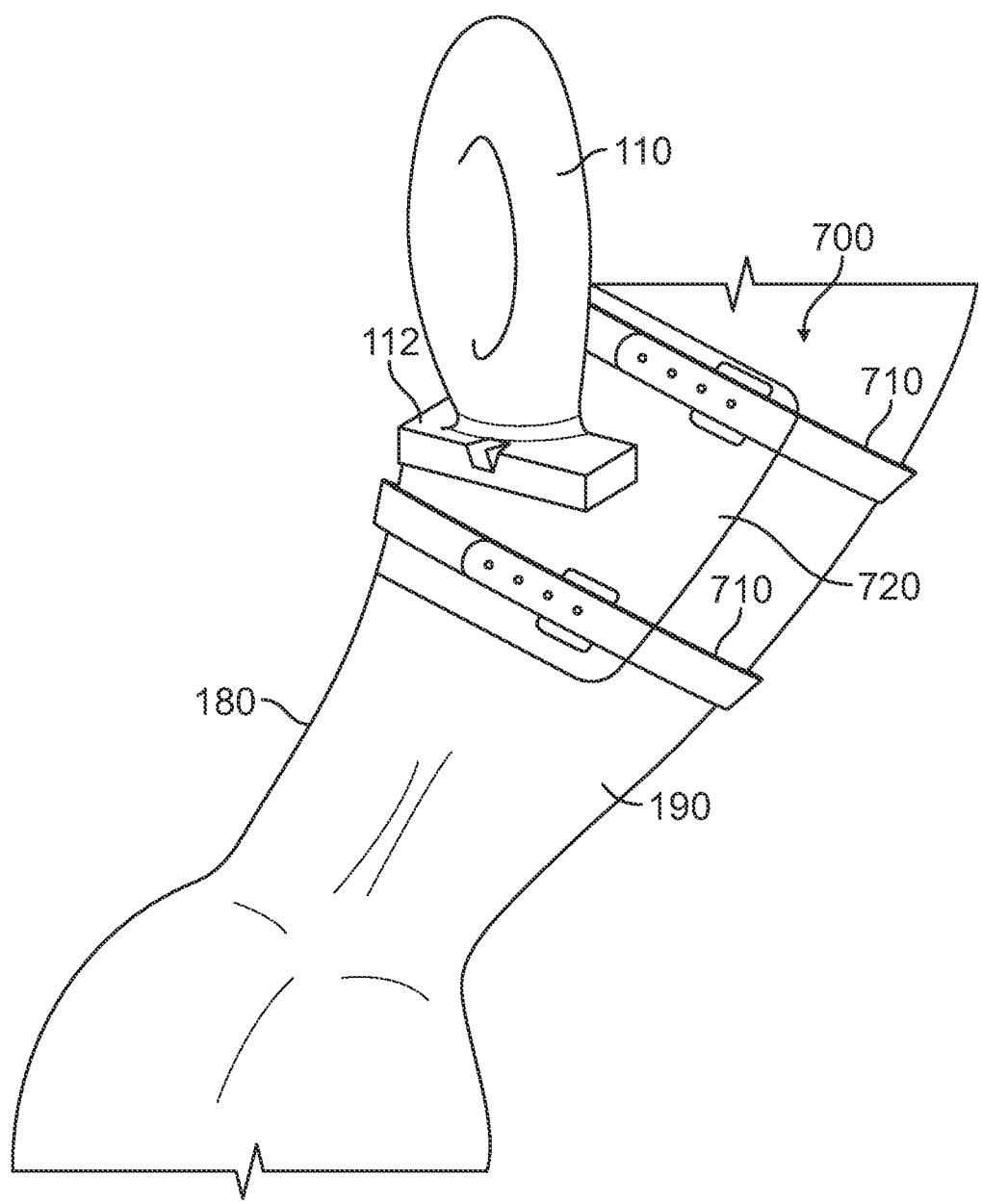
FIG. 7 provides a view of a securement device including straps in use with an ultrasound probe, in accordance with some embodiments.

Referring to FIG. 7, a securement device 700 including one or more straps 710 is shown in accordance with some embodiments. The securement device 700 may include a pad portion 720 to couple the straps to the probe head 112. In use, the pad portion 720 may be disposed between the probe head and the skin 190. The pad portion 720 may comprise an acoustic coupling material to acoustically couple the probe head 112 to the skin 190. In some embodiments, the pad portion 720 comprises an opening for the probe head 112 to pass through so that the probe head 112 can contact the skin 190 directly. The straps 710 may be configured to wrap around a patient extremity 180. The straps 710 may comprise one or more fastening components, such as a buckle, a latch, a hook and loop system, or any components suitable for attaching a strap 710 to itself or the pad portion 720. The straps 710 may be flexible and/or stretchable. The securement device 700 may include 1, 2, 3, or more straps 710. In some embodiments, the straps 710 may be configured to attach directly to the skin via an adhesive. In some embodiments, the straps 710 may be attached directly to the ultrasound probe 110, in which embodiment, the pad portion 720 may be omitted.

Each of the securement devices 200, 300, 400, 500, 600, and 700 shown and described above may be combined with any of the embodiments of the ultrasound probe 110 as shown in FIGS. 1A-1E.

Figure 8:
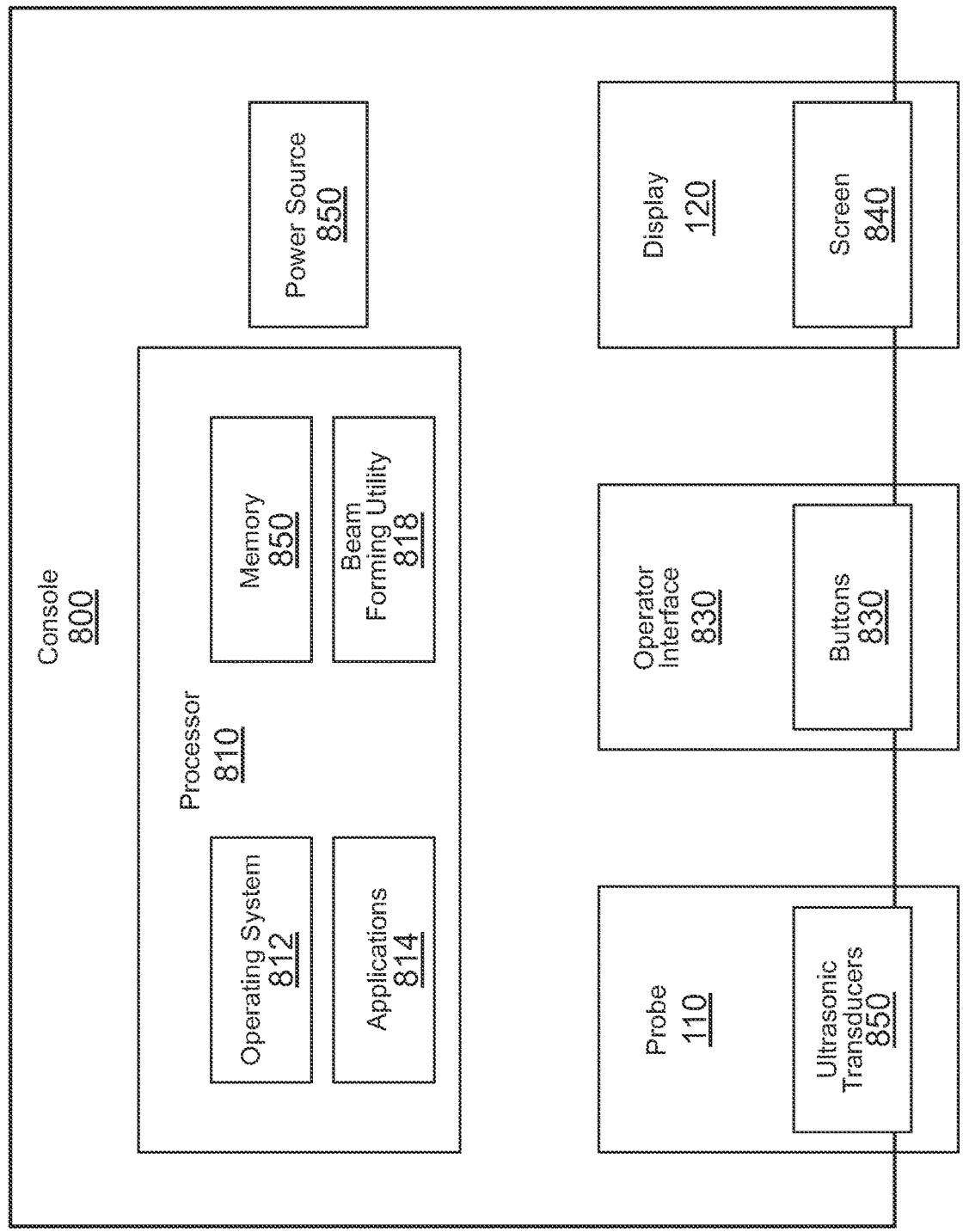
FIG. 8 provides a block diagram of a console of an ultrasound imaging system, in accordance with some embodiments.

Referring to FIG. 8, a block diagram of an ultrasound imaging system 100 (any of FIGS. 1A-1E) including a console 800 is shown in accordance with some embodiments. The console 800 may be integral to the ultrasound probe 110 or coupled to the ultrasound probe 110. Similarly, the console 800 may be integral to the display 120 or coupled to the display 120. In some embodiments, the console 800 may be integral to the display 120 and the ultrasound probe 110. The ultrasound probe 110 comprises one or more ultrasound transducers 820 and the display 120 includes a screen 840. The console 800 of the ultrasound imaging system 100 includes a processor 810 for governing system functionality by employment of a general-purpose operating system 812, memory 816, and applications 814 that may be stored in the memory 816 and executed by the processor 810. The memory 816 may include a non-transitory computer storage medium. The applications 814 may include a user interface 115 to allow a user (i.e., a clinician or a doctor) to operate the ultrasound imaging system 100. A beam forming utility 818, including suitable circuitry is also controlled by the processor 810 to enable ultrasound signals to be produced, received, and processed. For example, the beam forming utility 818 may produce some signals that may be reflected and received by the one or more ultrasound transducers 820.

The one or more ultrasound transducers 820 pass these signals into an area of a patient and receive reflected ultrasonic signals. The beam forming utility 818 may process the reflected ultrasonic signals converted into electric signals by the one or more ultrasound transducers 820 and may convert the electric signals into image data. The image data is passed on to the display 120 to be viewed by a user (i.e., a clinician) on the screen 840. The operator interface 115 may include buttons 830 including a power button and control buttons for operation of the ultrasound imaging system 100. Note that the console 800 can include different, fewer, or more components than those listed here, including those components that enable the ultrasound imaging system 100 to operate in a wireless networked manner with other local or remote image processing devices.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A system, comprising:
an ultrasound probe including a display pivotably coupled therewith; and
a securement device configured to secure the ultrasound probe to a patient, the securement device comprising a container in a form of a bag, the container defining an interior space filled with a gel, the interior space divided into an inner compartment and an outer compartment extending radially outward from the inner compartment, wherein the inner compartment and the outer compartment:
are separated by a wall of the container, and
each include an external surface configured to contact the patient, the container including:
a probe coupling mechanism configured to couple the ultrasound probe to the securement device, the probe coupling mechanism including the inner compartment defining a central depression configured to receive at least a portion of a probe head of the ultrasound probe; and a patient coupling mechanism configured to couple the securement device to the patient.

2. The system of claim 1, wherein, during use, ultrasound signals from the ultrasound probe pass through the securement device into the patient.

3. The system of claim 1, wherein the securement device is configured to constrain the ultrasound probe in an established location with respect to the patient.

4. The system of claim 1, wherein the securement device is configured to constrain the ultrasound probe in an established orientation with respect to the patient.

5. The system of claim 1, wherein the securement device is configured to maintain acoustic coupling of the ultrasound probe with the patient during ultrasound imaging of a blood vessel.

6. The system of claim 1, wherein the securement device is configured to maintain acoustic coupling of the ultrasound probe with the patient during insertion of a medical device into a blood vessel.

7. The system of claim 1, wherein the gel within the inner compartment is an acoustic coupling material configured to facilitate transmission of ultrasound signals through the securement device.

8. The system of claim 1, wherein the container comprises a frictional outer surface configured to inhibit sliding displacement of the ultrasound probe with respect to the securement device, and to inhibit sliding displacement of the securement device with respect to the patient.

9. The system of claim 1, wherein the gel within the outer compartment includes elevated density material to facilitate coupling of the securement device to the patient via a gravitational force, the elevated density material having a density between about 0.5 and 1.0 g/ml, between about 1.0 and 1.5 g/ml, between about 1.5 and 2.0 g/ml, or greater than about 2.0 g/ml.

10. The system of claim 9, wherein the elevated density material includes a density between about 1.5 and 2.0 g/ml, or greater than about 2.0 g/ml.

11. The system of claim 1, wherein the container is formed of a urethane polymeric material.

12. The system of claim 1, wherein the outer compartment extends radially outward beyond an outer perimeter of the ultrasound probe, the outer compartment configured to contact the patient beyond the outer perimeter.

13. The system of claim 1, wherein the container is configured to conform to a contour of the patient.

* * * * *